(12) United States Patent
Davis

(10) Patent No.: US 7,736,297 B2
(45) Date of Patent: *Jun. 15, 2010

(54) TINNITUS REHABILITATION DEVICE AND METHOD

(75) Inventor: Paul Benjamin Davis, Fremantle (AU)

(73) Assignee: Neuromonics Pty Limited, Chatswood, New South Wales (AU)

( * ) Notice: Subject to any disclaimer, the term of this patent is extended or adjusted under 35 U.S.C. 154(b) by 1541 days.

This patent is subject to a terminal disclaimer.

(21) Appl. No.: 10/682,894

(22) Filed: Oct. 14, 2003

(65) Prior Publication Data

US 2004/0131200 A1 Jul. 8, 2004

Related U.S. Application Data

(63) Continuation of application No. 09/936,687, filed as application No. PCT/AU00/00207 on Mar. 17, 2000, now Pat. No. 6,682,472.

(30) Foreign Application Priority Data

Mar. 17, 1999 (AU) .................................... PP 9275

(51) Int. Cl.
*H04R 25/00* (2006.01)
(52) U.S. Cl. ....................... 600/25; 381/73.1
(58) Field of Classification Search .................. 600/25, 600/559; 607/55, 59; 381/313, 312, 23.1, 381/317, 314, 320, 71.1–73.1
See application file for complete search history.

(56) References Cited

U.S. PATENT DOCUMENTS 3,023,388 A  2/1962  Di Girolamo et al.
4,222,393 A  9/1980  Hocks et al.

(Continued)

FOREIGN PATENT DOCUMENTS

CN  1349727  5/2002

(Continued)

OTHER PUBLICATIONS

Vernon et al. "Tinnitus masking: Unresolved problems" *Tinnitus* (1981) 239-262.

(Continued)

*Primary Examiner*—John P Lacyk
(74) *Attorney, Agent, or Firm*—Jones Day

(57) ABSTRACT

A tinnitus method and device for providing relief to a person suffering from the disturbing effects of tinnitus is described. The method can be implemented entirely in software to spectrally modify an audio signal in accordance with a predetermined masking algorithm which modifies the intensity of the audio signal at selected frequencies. A predetermined masking algorithm is described which provides intermittent masking of the tinnitus wherein, at a comfortable listening level, during peaks of the audio signal the tinnitus is completely obscured, whereas during troughs the perception of the tinnitus occasionally emerges. In practice it has been found that such intermittent masking provides an immediate sense of relief, control and relaxation for the person, while enabling sufficient perception of the tinnitus for habituation and long term treatment to occur. Advantageously the predetermined masking algorithm is specifically tailored to the audiometric configuration of the person. For example, the masking algorithm may be partly tailored to the hearing loss characteristic of the person. A tinnitus rehabilitation device used in conjunction with a personal sound reproducing system is also described.

39 Claims, 11 Drawing Sheets

U.S. PATENT DOCUMENTS

| | | | |
|---|---|---|---|
| 4,254,922 | A | 3/1981 | Wolf et al. |
| 4,947,432 | A | 8/1990 | Pholm |
| 4,972,487 | A | 11/1990 | Mangold et al. |
| 4,984,579 | A | 1/1991 | Burgert et al. |
| 5,024,612 | A | 6/1991 | Van den Honert et al. |
| 5,167,236 | A | 12/1992 | Junker |
| 5,226,086 | A | 7/1993 | Platt |
| 5,279,292 | A | 1/1994 | Baumann et al. |
| 5,303,306 | A | 4/1994 | Brillhart et al. |
| 5,325,872 | A | 7/1994 | Westermann |
| 5,403,262 | A | 4/1995 | Gooch |
| 5,481,645 | A | 1/1996 | Bertino et al. |
| 5,628,330 | A | 5/1997 | Upham |
| 5,697,975 | A | 12/1997 | Howard, III et al. |
| 5,735,885 | A | 4/1998 | Howard, III et al. |
| 5,788,656 | A | 8/1998 | Mino |
| 5,795,287 | A | 8/1998 | Ball et al. |
| 5,961,443 | A | 10/1999 | Rastatter et al. |
| 6,041,129 | A | 3/2000 | Adelman |
| 6,047,074 | A | 4/2000 | Zoels et al. |
| 6,048,305 | A | 4/2000 | Bauman et al. |
| 6,077,215 | A | 6/2000 | Leysieffer |
| 6,115,478 | A | 9/2000 | Schneider |
| 6,155,971 | A | 12/2000 | Calhoun et al. |
| 6,198,971 | B1 | 3/2001 | Leysieffer |
| 6,307,945 | B1 | 10/2001 | Hall |
| 6,379,314 | B1 | 4/2002 | Horn |
| 6,682,472 | B1 * | 1/2004 | Davis .......................... 600/25 |
| 2006/0020161 | A1 | 1/2006 | Mageras et al. |

FOREIGN PATENT DOCUMENTS

| | | |
|---|---|---|
| EP | 0820211 | 1/1998 |
| GB | 2134689 | 8/1984 |
| GB | 2235349 | 2/1991 |
| JP | S62-66557 | 4/1987 |
| JP | H10-80000 | 3/1998 |
| WO | WO87/07464 | 12/1987 |
| WO | WO 99/49822 | 10/1999 |
| WO | WO 00/21440 | 4/2000 |
| WO | WO 00/41440 | 7/2000 |
| WO | WO 00/56120 | 9/2000 |
| WO | WO 02/062264 | 8/2002 |
| WO | WO 2005/053533 A1 | 6/2005 |

OTHER PUBLICATIONS

Al-Jassim "The use of Walkman mini-stereo system as a tinnitus masker" *Journal of Laryngology and Otology* (Jan. 1988) vol. 102, pp. 27-28.

User and Service Manual for Sony, Models TCB-D8 and D-171, 1995 and 1996. Available at www.sony.net and www.sony.com.

International Search Report for related International Application No. PCT/AU2004/001700 dated Feb. 1, 2005.

Australian Search Report and Written Opinion for related Application No. SG 20063732-9 dated Apr. 21, 2008.

First Office Action for related Chinese Application No. 200480041291.3 dated Oct. 26, 2007.

Office Action for related Japanese Application No. 2000-605446 dated Dec. 4, 2007.

* cited by examiner

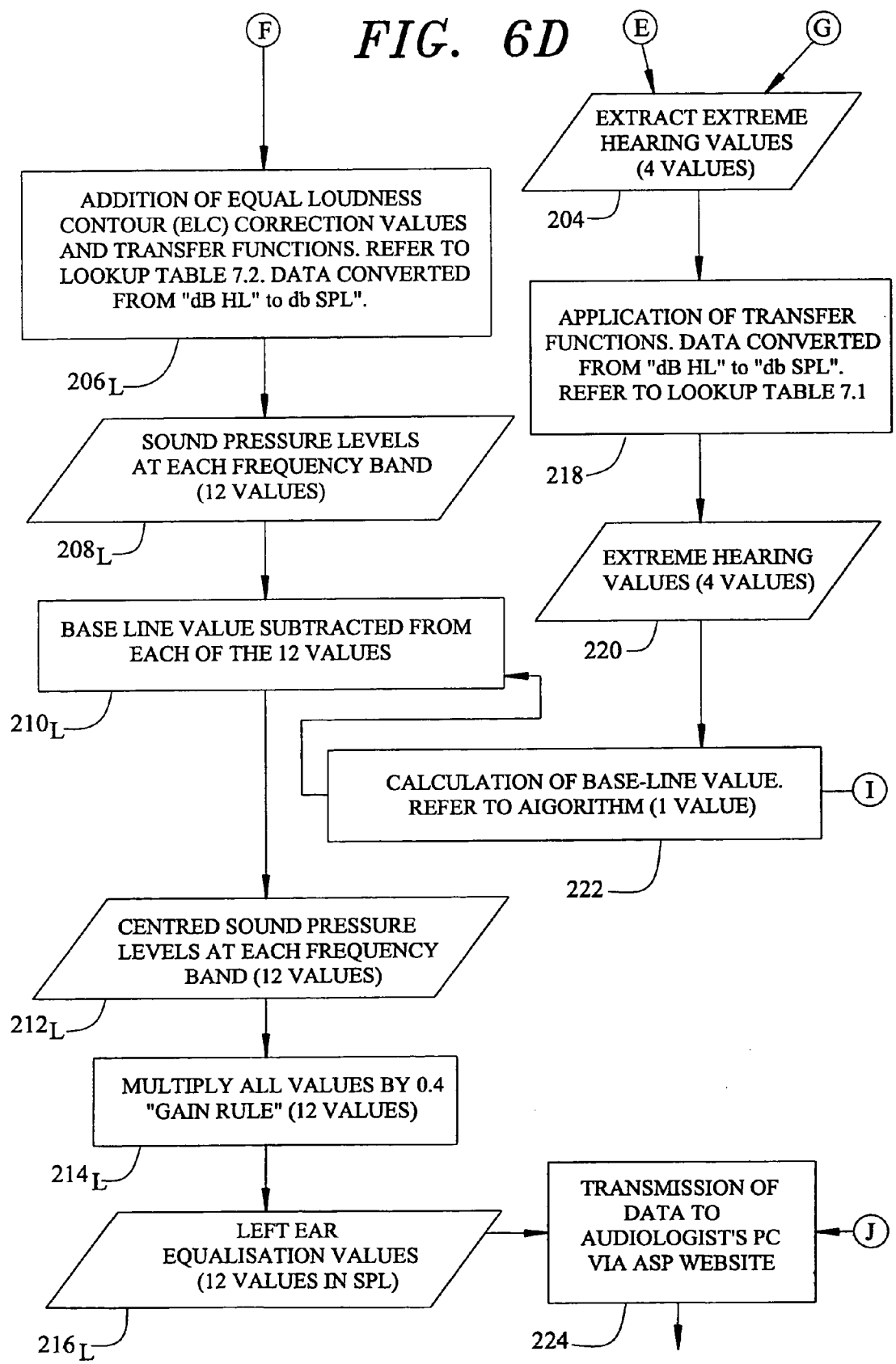

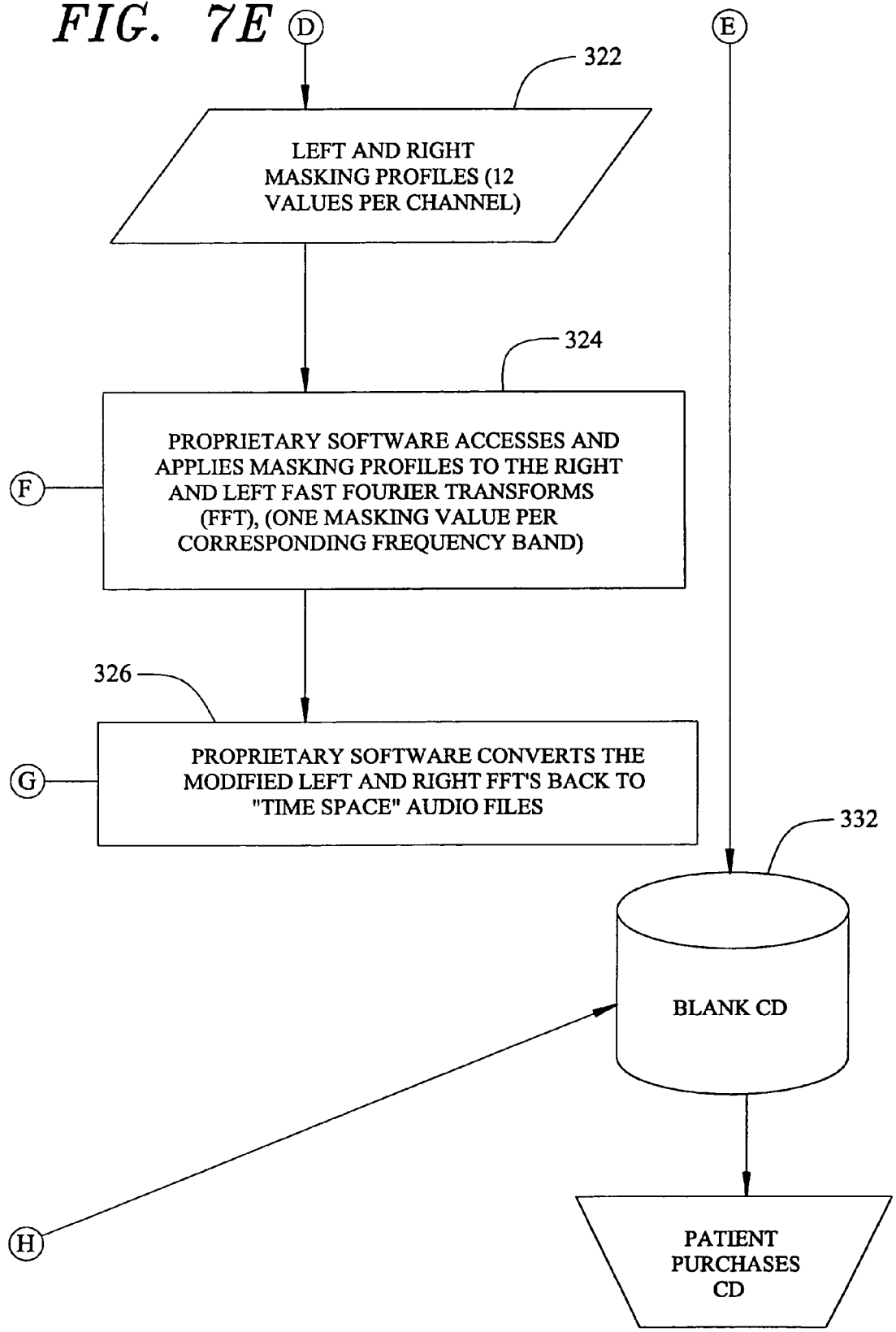

TINNITUS REHABILITATION DEVICE AND METHOD

CROSS REFERENCE TO RELATED APPLICATION

This application is a continuation of U.S. Ser. No. 09/936,687, filed Sep. 17, 2001, now U.S. Pat. No. 6,682,472 which is the National Phase application of International Application No. PCT/AU00/00207, filed Mar. 17, 2000, which designates the United States. These applications, in their entirety, are incorporated herein by reference.

FIELD OF THE INVENTION

The present invention relates to a tinnitus rehabilitation device and method for providing relief and treatment to persons suffering from the disturbing effects of tinnitus and relates particularly, though not exclusively, to such a method and device that employs intermittent masking of the tinnitus.

BACKGROUND TO THE INVENTION

Tinnitus is the perception of a sound in the absence of any corresponding external sound. It is most commonly perceived as a ringing, buzzing, whirring type sound, but can also be perceived as a beating, or pounding sensation. Around one third of people who suffer from tinnitus can be quite highly disturbed by it. Continuous perception of tinnitus can lead to insomnia, an inability to relax, state and trait anxiety, depression, and even suicide in extreme cases. Often closely associated with tinnitus is the perception of hyperacusis, which is a great intolerance to external sounds, even the softer everyday sounds. This distressing condition can even occur as a precursor to tinnitus, and is thought to share the same underlying causes. Thus, every reference to tinnitus in this document should be construed as including the phenomena of hyperacusis or other types of loudness discomfort.

There are very few effective treatment options available for tinnitus sufferers, with the vast majority only being advised that "you'll have to learn to live with it". Most patients find that they can far more readily ignore an external sound than their tinnitus. One palliative method has been to use hearing aid-style devices that produce a band of noise to totally mask the perception of the tinnitus. This gives a sense of relief and control over the tinnitus in around half of patients, but usually has no long-term effect. The prohibitive cost (around A$1500) and aesthetic considerations limits the proportion of sufferers for whom this is a viable measure. The presence of hearing loss for external sounds in the tinnitus region often means that the masking noise needs to be unpleasantly loud before the tinnitus can be masked, and the noise is often judged to be not much better than the tinnitus itself.

In the past four years, a new understanding of the neurophysiological processes underlying tinnitus has been published, emphasising the role of the neural pathways in the emergence of distressing tinnitus and the possibility of using this neural plasticity to retrain its perception. This has been dubbed "Tinnitus Retraining Therapy" or TRT. In this technique, patients are given intensive counselling, and use noise generators at a volume that does not completely mask the tinnitus. Long term reductions in tinnitus disturbance have been achieved in some patients, but it is usual for this process to take at least 18 months of therapy before any substantial benefit occurs. TRT also offers very little immediate sense of relief from the tinnitus, and no relief from the associated sleep disturbance and inability to relax.

The closest known prior art to the invention is the "Silentia Set" developed by Starkey Corp., which is a pair of hearing aid devices which wirelessly receive signals from a stereo system via an induction loop under a pillow at bedtime. Recording of high frequency noise bands ("water sounds"), babble noise, traffic sounds and music have been used to mask tinnitus using this system, however the high cost of the Silentia Set make it prohibitive for many sufferers.

Other prior art audiotherapeutic techniques using music are the Tomatis Method developed by Alfred A. Tomatis, and Auditory Integration Training. While neither method is designed for the treatment of tinnitus, the two techniques have some similarities in that they modify music for the treatment of auditory disorders. The Tomatis Method employs an "Electronic Ear" developed by Alfred Tomatis, (U.S. Pat. No. 4,021,611). It has its origins from an extremely outdated model of how the auditory system works, and has been widely debunked by audiological organisations. Auditory Integration Training is based on the Tomatis Method, but presents the music at extremely loud levels, that may result in hearing damage, and importation of devices using this technique have been banned by the American Food and Drug Administration.

SUMMARY OF THE INVENTION

The present invention was developed with a view to providing a more effective rehabilitation technique and device for tinnitus sufferers that is consistent with contemporary understandings of the underlying pathology in the auditory system, of which tinnitus is a symptom.

Throughout this specification the term "comprising" is used inclusively, in the sense that there may be other features and/or steps included in the invention not expressly defined or comprehended in the features or steps subsequently defined or described. What such other features and/or steps may include will be apparent from the specification read as a whole.

According to one aspect of the present invention there is provided a tinnitus rehabilitation method for providing relief to a person suffering from the disturbing effects of tinnitus, the method comprising:

providing an audio signal spectrally modified in accordance with a predetermined masking algorithm designed to modify the intensity of the audio signal at selected frequencies whereby, in use; when the spectrally modified audio signal is heard by the person it provides significant masking of the tinnitus.

Preferably the method further comprises the steps of:

transmitting, using a computer, data representing an audiogram of the person suffering from tinnitus;

processing said audiogram data at a remote location and producing required equalisation response data based on said audiogram data using said predetermined masking algorithm;

receiving, using a computer, said required equalisation response data; and, combining said required equalisation response data with audio data representing said audio signal to produce said spectrally modified audio signal.

According to a second aspect of the invention there is provided a method of using a computer to provide access to a predetermined masking algorithm used in tinnitus rehabilitation, for providing relief to a person suffering from the disturbing effects of tinnitus, the method comprising:

receiving on-line, from a user, data representing an audiogram of the person suffering from tinnitus;

processing said audiogram data using said predetermined masking algorithm to produce required equalisation response data based on said audiogram data; and, transmitting said required equalisation response data to the user.

According to a another aspect of the present invention there is provided a tinnitus rehabilitation sound recording for providing relief to a person suffering from the disturbing effects of tinnitus, the sound recording comprising:

an audio signal spectrally modified in accordance with a predetermined masking algorithm designed to modify the intensity of the audio signal at selected frequencies whereby, in use, when the sound recording is heard by the person it provides significant masking of the tinnitus.

Preferably the predetermined masking algorithm provides intermittent masking of the tinnitus wherein at a comfortable listening level, during peaks of the audio signal the tinnitus is substantially completely obscured, whereas during troughs the perception of the tinnitus occasionally emerges. In practice it has been found that such intermittent masking can provide an immediate sense of relief, control and relaxation for the person, whilst enabling sufficient perception of the tinnitus for habituation and long term treatment to occur.

Typically said predetermined masking algorithm is designed to modify the intensity of the audio signal across substantially the full spectral range of the audio signal. Preferably said audio signal is a highly dynamic signal in which the spectral content and intensity constantly varies over time. Most preferably the audio signal is a music signal. However other types of signals including speech or noise might also be employed.

Advantageously said predetermined masking algorithm is at least partly tailored to the audiometric configuration of the person. Typically said predetermined masking algorithm is partly tailored to the hearing loss characteristic of the person. Preferably the spectral qualities of the audio signal are modified by the masking algorithm so as to provide a relatively equal sensation level across a major portion of the audio spectrum in both ears. Typically said predetermined masking algorithm also incorporates a set of calibration figures such as for converting dB HL (Hearing Level) to dB SPL (Sound Pressure Level), or to correct for the presence of various coupling system types.

According to a still further aspect of the present invention there is provided a tinnitus rehabilitation device for providing relief to a person suffering from the disturbing effects of tinnitus the device comprising:

signal filtering means adapted to spectrally modify an audio signal in accordance with a predetermined masking algorithm designed to modify the intensity of the audio signal at selected frequencies whereby, in use, when the spectrally modified audio signal is heard by the person it provides significant masking of the tinnitus.

Preferably said signal filtering means is a programmable signal filtering means whereby, in use, the device can be programmed with a predetermined masking algorithm adapted to the particular needs of the individual suffering from tinnitus.

In a preferred embodiment of the device the predetermined masking algorithm is of the form:

| | |
|---|---|
| REQ = | M(SPL + ELC(0.25, 0.5, 1, 2, 3, 4, 6, 8, 10, 12 kHz) - Baseline) |
| where REQ = | Required equalisation response of the Tinnitus Retraining Protocol |
| Baseline = | 0.5 (A − B) + B |
| A = | mean dB SPL at the two adjacent greatest hearing loss frequencies in the greatest hearing loss ear |
| B = | mean dB SPL at the two adjacent least hearing loss frequencies in the least hearing loss ear |
| SPL = | hearing thresholds (in dB HL) converted to dB SPL |
| ELC = | transfer values for 40 Phon Equal Loudness Contours |
| M = | gain multiplier = 0.3 to 0.95 |
| Preferably M = | 0.4 |

However, in an alternative software embodiment of the invention, the mathematical algorithm by which the individual prescription of the audio signal is calculated may differ from the above algorithm. Such other embodiments of the invention would be consistent with the essential clinical technique that is intended to provide a modification of the intensity of an audio signal to account for hearing levels specifically for the relief and/or treatment of tinnitus and hyperacusis.

Preferably the device is employed in conjunction with a personal music player (PMP) and has an input adapted to connect to the audio output headphone jack on the PMP. Preferably the device has a standard headphone jack to which a standard PMP headphone can be connected. Alternately, a transmitter may be used to transmit a signal to a wireless type of receiver that may be placed in the ear canal, concha area, behind the ear, or some other area relatively close to the ear.

BRIEF DESCRIPTION OF THE DRAWINGS

In order to facilitate a more detailed understanding of the nature of the invention preferred embodiments of the tinnitus rehabilitation device and method will now be described in detail, by way of example only, with reference to the accompanying drawing in which.

DETAILED DESCRIPTION OF PREFERRED EMBODIMENTS

Tinnitus masking can be broadly defined as the obscuring of tinnitus perception with an external sound. Hearing aids can provide an effective form of environmental noise masking for only around 10% of sufferers. The most reliable audiometric measure of the effectiveness of tinnitus maskers is the amount of noise required to just mask an individual's tinnitus. This measure is known as the Minimum Masking Level ("MML"). Amongst the most important criteria for successful masking is that the acceptability of a masking stimulus is inversely proportional to its MML, and that the stimulus needs to be a sufficiently pleasant substitute for the tinnitus. In the present inventor's clinical practice, several sufferers have reported attempting to use music to find relief from their tinnitus, but often found that the volume required to mask their tinnitus was unacceptably high. Most of these persons tended to have a steeply sloping hearing loss characteristic, and a tinnitus pitch which closely corresponded with the edge of the maximal hearing loss frequencies. One of the reasons why previous attempts at using music have not always been successful may be the extremely high co-morbidity of high frequency hearing loss with tinnitus.

Figure 1:
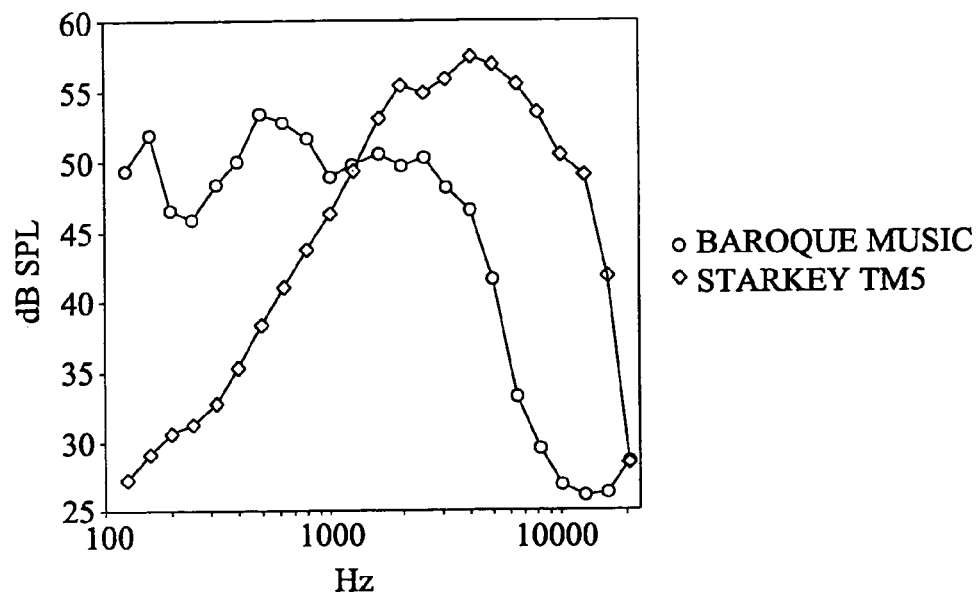
FIG. 1 is a graphical representation of the long-term spectra of both a music recording and a typical prior art tinnitus masker.

Typically, the presence of a sloping high frequency hearing loss would mean that at a relaxing sound volume level, only the low pitch components of the music are heard, and therefore the perception of any musicality and high frequency available for masking is inhibited. The long term spectra of both a music recording and a typical prior art tinnitus masker (a Starkey TM5) are illustrated in FIG. 1. A sound level analyser was used to average the response of each of the two recordings over a 64 second period. The spectra were then matched at 1 kHz to enable a comparison of the frequency composition of the two spectra, irrespective of overall sound pressure-levels. As can be seen from FIG. 1, if the masker is assumed to be the optimal frequency response for hearing impaired listeners, then the unfiltered music has insufficient high frequency energy and excessive low frequency response. Therefore, the present inventor has developed a tinnitus masking protocol which modifies the frequency response characteristics of an audio signal with a view to overcoming some of the shortcomings of traditional tinnitus maskers.

Although the following description will be made primarily with reference to modifying the frequency response characteristics of music, it is to be understood that a tinnitus masking protocol in accordance with the invention may also be applied to other types of audio signal suitable for masking of tinnitus, or for providing auditory stimulation for tinnitus and hypercusis therapy without masking. Furthermore, in view of the relatively high cost of traditional hearing aid-style maskers, the following description will give particular emphasis to the use of conventional, insert or wireless headphone systems or insert type headphones in conjunction with a suitable personal sound reproduction system such as a high fidelity personal music player (PMP) for audio cassette, CD or MP3 recordings. In Australia, the retail cost of a high fidelity PMP is around one-tenth the cost of conventional binaural maskers. However, it is to be understood that the tinnitus masking protocol according to the invention may also be applicable to conventional hearing aid-style maskers. The technique can also be applicable to the setting of additional user programs in hearing aids, or the modified signal may be transmitted to the tinnitus sufferer through their hearing aids' telecoil or induction coil facility.

In addition to the low cost and high portability of PMPs, they generally possess small headphones with long-throw transducers that enable far superior fidelity compared to most free field loudspeaker systems. Furthermore, headphones are generally more effective than loud speakers because they circumvent the extensive attenuation of high frequency sounds that occurs through a free field. Changes in PMP earphone position on the pinna have been shown to have very limited effects on the spectral composition of toned sweeps measured in a KEMAR (Knowles Electronic Mannequin for Acoustic Research).

In developing a tinnitus masking protocol, the required extended upper frequency stimulus presented challenges for the conversion of audiogram results to the required real ear response, given that there are as yet no internationally agreed-upon standards for the conversion between dB HL to dB SPL for 10 and 12 kHz pure tone and narrow band noise stimuli. The manufacturer's calibration specifications for a Madsen OB 822 audiometer were used to extrapolate the required values for use with a telephonics TDH 39 headphones and MX 41/AR cushions. The audiometer was professionally calibrated accordingly. The values for 10 kHz were 50 dB HL=59.5 dB SPL and at 12 kHz, 50 dB HL=61 dB SPL. All ISO hearing level frequencies below 10 kHz were calibrated as per the relevant Australian standards (AS 1591.2-1987). Table 1 lists the transfer/calibration values in inverted format used for converting dB HL to dB SPL.

TABLE 1

| | Frequency | | | | | | | | | |
|---|---|---|---|---|---|---|---|---|---|---|
| kHz | 0.25 | 0.5 | 1 | 1.5 | 2 | 3 | 3 | 6 | 8 | 10* | 12* |
| dB | 25.5 | 11.5 | 7.0 | 6.5 | 9.0 | 10.5 | 10.5 | 16.5 | 12.0 | 9.5 | 11.0 |

A further feature of the first tinnitus masking protocol (TMP1) developed by the inventor, was an adaptation of the half gain rule, whereby amplification for hearing loss is most effective when it compensates for only around one half of the hearing deficit. This rule underlies most current hearing aid prescriptive practices. The TMP1 attempted to maximise the acoustic energy centred around the pitch of the individual's tinnitus, and to "balance" the headphone output to correct for any asymmetrical hearing loss. A further goal was to enable the balanced perception of the masking stimulus throughout the person's head, rather than at the ear level like traditional uncorrelated tinnitus maskers.

All PMPs have a volume control range that far exceeds what is available in hearing aids, and so the TMP1 did not need to specify absolute gain figures. However, PMPs generally do not possess a left/right balance control, and this was expected to reduce their acceptability in cases of asymmetrical hearing loss and its associated loudness recruitment As the TMP1 formulae aimed to minimise the perceptual loudness of the music or noise required to mask an individual's tinnitus, it thus only needed to specify the relative frequency response characteristics for each ear when presented in those reproduction systems that do not provide individual control of each stereo channel.

The procedure for applying the TMP1 was thus as follows:
(i) The individual's pure tone hearing level thresholds at each frequency were converted to dB SPL by the addition of the transfer values in Table 1.
(ii) The tinnitus pitch match frequency in the most severely affected ear was chosen for the maximal point of the base line calculation. The two adjacent best hearing thresholds of the lesser hearing loss ear was always chosen as the minimum point of the calculation. When a reliable pitch match was not found using pure tones, it was substituted with the mean of the two adjacent best hearing frequencies. Thus, the base line constituted a mid line value between the two greatest audiometric extremities.

(iii) The final equalisation values were then derived by subtracting the base line from the hearing threshold (expressed in dB SPL) for each frequency and each ear. Thus the algorithm for patients whose tinnitus pitch could not be reliably determined was:

Baseline=$0.5(A-B)+B$

Required Equalisation, REQ=$0.5$ {$SPL_{(0.25, 0.5, 1, 2, 3, 4, 6, 8, 10, 12\ kHz)}$−Baseline}

The algorithm for non-tonal tinnitus was:

Baseline=$0.5(C-B)+B$

REQ=$0.5${$SPL_{(0.25, 0.5, 1, 2, 3, 4, 6, 8, 10, 12\ kHz)}$−Baseline}

Wherein,

A=hearing threshold (dB SPL) at frequency of tinnitus pitch match.

B=mean dB SPL at the 2 adjacent least hearing loss frequencies.

C=mean dB SPL at the 2 adjacent greatest hearing loss frequencies.

Example 1

Figure 2:
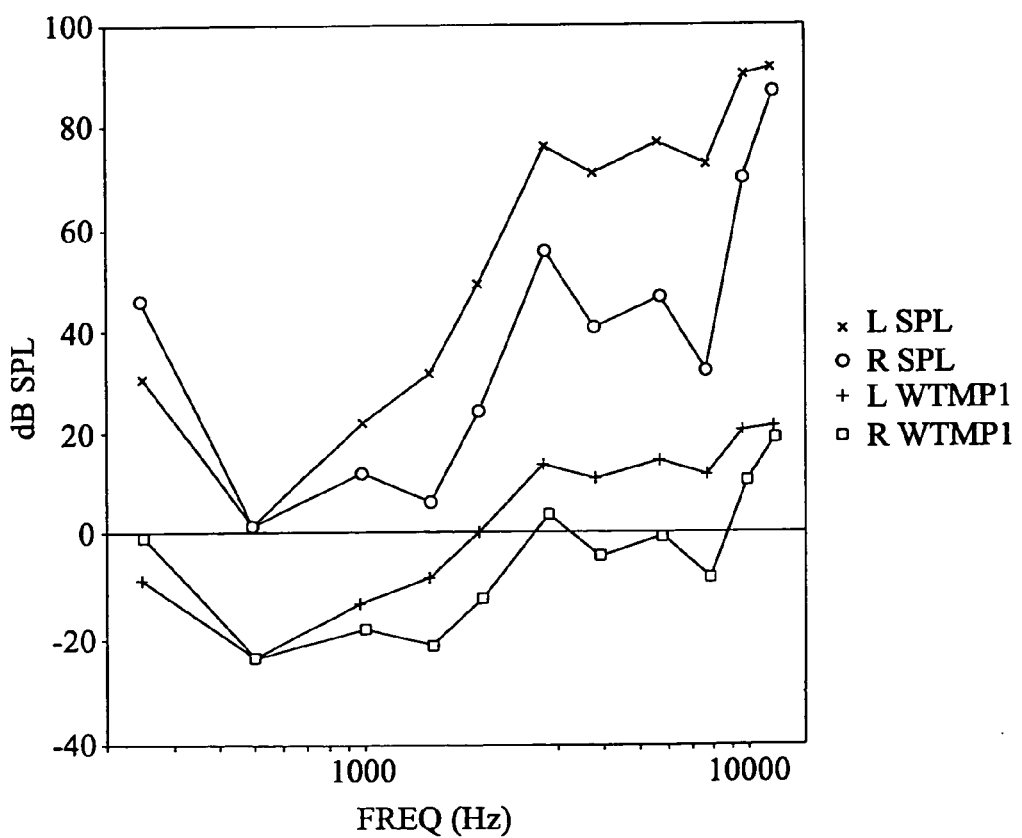
FIG. 2 is a graphical representation of a typical patient's hearing thresholds and their required equalisation curve calculated using a first embodiment of the masking algorithm.

FIG. 2 is a graphical representation of the relationship between a typical individual's hearing levels, tinnitus and their required TMP1 equalisation curves. This individual has a steeply sloping high frequency bilateral hearing loss and tinnitus at 10,000 Hz, both greater on the left side. Consequently, the required equalisation curves revolve around the equaliser's baseline, achieving a partial correction for hearing loss by boosting the amount of high frequency gain and also correspondingly attenuating the low frequencies. As the hearing loss and tinnitus is worse on the left, that ear receives correspondingly greater amplification. Because of the abnormal growth of loudness perception which usually accompanies sensorineural hearing loss, (recruitment, and/or the presence of hyperacusis), complete correction for hearing levels is not provided, as this may exceed the individual's loudness discomfort levels.

A tinnitus rehabilitation sound recording was then produced on an audio cassette tape for use in the individual's PMP. A stereo frequency equaliser (Genexxa 31-9082) was used in this procedure, which includes ten adjustable frequency bands per channel, with centre frequencies at 0.031, 0.062, 0.125, 0.25, 0.5, 1, 2, 4, 8, 16 kHz. Each control had a range of + or −12 dB SPL. The equaliser featured an "EQ record" facility, so that the audio signal could be passed through the equaliser circuit before being recorded. The equaliser's controls for each of the ten frequency bands was set to the calculated values for the left ear in the left channel of the equaliser, and the right ear values set in the right channel, in accordance with the particular individual's equalisation values as calculated by the TMP1 algorithm. The stereo output from a broadcast quality cassette recorder was connected to the stereographic equaliser, which then had its output routed to another high fidelity cassette deck for recording onto high fidelity audio cassette tape. Dual leads and stereo RCA connecters were used to preserve L/R channel separation.

Modified sound recordings of both music and white noise were made for use in clinical trials with 30 participants. Each participant was counselled as to the rationale behind masking therapy and the possible benefits of using the tinnitus rehabilitation sound recording. Each participant was issued with a new PMP with standard insert headphones (Sony MDR E552) that fit into the concha and thus do not require a headband. Sound level-peak analysis measures were then performed. With their custom-made tape playing in the PMP, they were asked to slowly turn up the volume until they could just no longer perceive their own tinnitus. This level was marked on the volume control wheel. Each participant was told to notify the audiologist if they subsequently needed to turn up the volume further than the marked position. They were encouraged to experiment downwards with the volume control over the course of each masking session, as they might find that they require progressively less volume to totally mask if residual inhibition occurred.

One group of participants was given a noise tape whereas the other group was given a music tape. While both treatment groups has similar levels of pre-therapy distress associated with their tinnitus, the music group displayed a much greater improvement by mid-therapy and these gains were maintained at the two-year post-therapy follow up. The noise group also displayed some improvement, but much less dramatic then the music group. 96% of the participants found their music or noise tapes to be an effective masker, which is a far higher acceptance rate than for conventional ear level tinnitus maskers.

In some cases, the TMP1 appeared to present an unbalanced perception of loudness where the individual possessed a substantial inter-aural asymmetry. The real-ear perception of loudness may have deviated from the prescribed response due to perception of loudness differences at various points across the frequency range. It was also thought that the half gain rule for hearing aids might be best suited for the moderate hearing loss population, and that a mild hearing loss might only require one-third gain. Furthermore, it is possible that the recruitment of loudness phenomena might be greater in tinnitus patients than non-tinnitus patients, particularly given its high co-morbidity with hyperacusis and phonophobia (the fear of external sounds). These factors suggested that the TMP1 might be overcompensating for hearing loss, and that further modifications were required to optimise the procedure.

Figure 3:
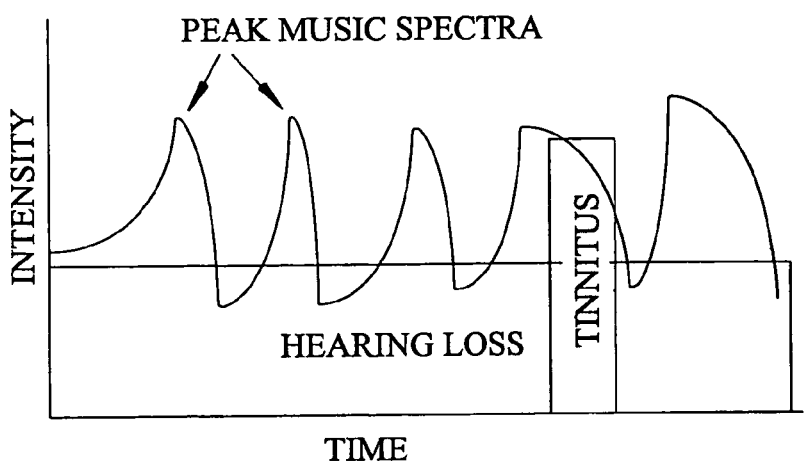
FIG. 3 is a schematic diagram graphically illustrating intermittent tinnitus masking with music.

The main purpose of the TMP1 algorithm was to produce an acceptable substitute for the tinnitus at the lowest possible. MML and to accommodate for any interaural symmetries. However, it was subsequently realised that an improved masking algorithm would be more robust if the prescription of the required equalisation response was performed solely on the basis of maximum and minimum hearing levels, and thereby attempt to provide relatively equal sensation levels at all frequencies. Data from the TMP1 study indicated that 44.4% of the music group, and 28.6% of the noise group participants preferred to set the volume of their audio tapes at a level which only partially masked their tinnitus. This occurred despite being instructed that the optimal setting was to totally mask. The differences in masking level preferences between the two types of stimuli also suggests that music was more acceptable than noise when used at volume levels where the tinnitus could still be partly perceived. Whilst the historical approach has been to totally mask tinnitus, and the current clinical trend is to partially mask, the present inventor has developed an improved tinnitus masking protocol based on intermittent masking. Since music is a highly dynamic signal, it appears possible that the intensity of music which partially masks might actually constitute a form of intermittent masking. A schematic representation of intermittent tinnitus masking using a music signal is illustrated in FIG. 3.

Without wishing to be bound by theory, it is believed that the intermittent masking of tinnitus with a relaxing stimulus (such as music) may be effective on a psychological, as well as on an acoustic or neural level. In theory, it is feasible that intermittent tinnitus masking with music might constitute a form of systematic desensitization. Whilst in a relaxed state, the listener might be alternatively perceiving, then not perceiving the tinnitus, according to the fluctuations in the peak levels of the music. The predicability of the music may mean that the tinnitus might not even be consciously perceived during the "troughs" of the music. Additionally, the tinnitus might "reappear" from the music often enough for habituation to occur. But the ongoing dynamic nature of the music signal prevents this limited exposure from being disturbing, and this may reduce any limbic system enhancement. Thus, the proposed intermittent-masking-with-relaxation-music technique may promote a synergetic effect through its additional mechanisms of facilitating a sense of control, a reduction in general anxiety levels, and a form of auto-hypnosis leading to a reduction of fear about the tinnitus itself. Therefore, an improved masking algorithm based on a tinnitus retraining protocol (CRP) was developed that was designed to produce intermittent masking of the tinnitus.

In practice, the TMP1 algorithm's use of the half-gain rule appeared to overcompensate for hearing loss as noted above, sometimes making the recording seem unbalanced or "tinny". Conversely, there were several factors that suggested that the one-third rule might not provide sufficient equalisation. The long term music spectrum has considerably less high frequency energy than what is typically available from conventional tinnitus maskers, and yet the greatest hearing loss is typically concentrated in this region (see FIG. 1). Therefore, any substantial reduction of gain could prevent achieving adequate high frequency equalisation to overcome the limitations in the music spectra and the effects of hearing loss. Therefore, because the half gain rule was sometimes excessive, but one third gain may be insufficient for the purposes of modifying music for long term tinnitus retraining, a medium selected by the incorporation of a 0.4 gain multiplier, (M).

To further facilitate the provision of equal sensation levels of music across the full spectral range of the music signal, the improved TRP algorithm adopted the ISO Equal Loudness Contours (ELC). The ELC transfer values correct for any differences in loudness perception depending on the discreet frequencies (International Standards Association, 1961). The 40 phon contour curve was selected because the earlier study found that the mean participant's customised music recordings, under total masking conditions, displayed a RMS of 45.7 dB SPL. Thus, with 8 dB representing an approximate doubling of perceived loudness, 37.7 dB was extrapolated to be the midpoint between the threshold and total masking, and thus representative of the intensity around which intermittent masking would occur with those with a mild to moderate sloping hearing loss. The 40 phon contour was thus utilised because it was the closest to this mid point, and choice of the lower value curve also helped compensate for loudness recruitment.

The standard audiometric procedure is to obtain hearing thresholds using TDH 39 headphones, and the results are expressed in dB HL (Hearing Level). However, the convention for specifying hearing aid characteristics is to utilise dB SPL (Sound Pressure Level) values. Consequently the hearing thresholds (dB HL) obtained in the 6 cm$^3$ headphones need to be converted into dB SPL by the addition of the transfer values in Table 1.

These transfer values were then summated with the 40 Phon contour values. The resulting transfer/calibration values are displayed in Table 2.

TABLE 2

| kHz | Frequency | | | | | | | | | | |
|---|---|---|---|---|---|---|---|---|---|---|---|
| | .25 | .5 | .75 | 1 | 1.5 | 2 | 3 | 4 | 6 | 8 | 10 | 12 |
| Corrections | 23.5 | 7.5 | 5.5 | 7 | 6.5 | 7 | 5.5 | 2.5 | 16.5 | 21 | 16.5 | 13 |

The tinnitus retraining protocol (TRP) algorithm is a modification of the TMP1 algorithm given on page 10 above, and is as follows:

$$REQ = 0.4\{ELC + SPL_{(0.25, 0.5, 1, 2, 3, 4, 6, 8, 10, 12\, kHz)} - Baseline\}$$

Where: Baseline = $0.5(A-B)+B$

A = mean dB SPL at the two adjacent greatest hearing loss frequencies in the greatest hearing loss ear.
B = Mean dB SPL at the two adjacent least hearing loss frequencies in the least hearing loss ear.
SPL = hearing thesholds (in dB HL), converted to dB SPL.
ELC = transfer values for 40 Phon Equal Loudness Contours.

Alternatively, the patient's hearing thresholds may be obtained using ⅓ octave narrow band noises, and the gain multiplier (M) becomes 0.7 (or between the range of 0.5 to 0.95).

The procedure for applying the TRP was as follows:
(i) The person's audiogram was perused to ascertain the two adjacent greatest hearing loss frequencies in the greatest hearing loss ear (A), and also the two adjacent least hearing loss frequencies in the least hearing loss ear (B).
(ii) These four dB HL values were then converted to dB SPL by the addition of the transfer values in Table 1 (on page 9).
(iii) The dB SPL mean of the two adjacent greatest hearing loss frequencies in the greatest hearing loss ear (A) was then calculated in dB SPL, and the procedure repeated for the two adjacent least hearing loss frequencies in the least hearing loss ear (B).
(iv) A midline value was then calculated by the subtraction of B from A, which value is then halved, and the result added to the B value. This is the TRP baseline.
(v) All of the dBHL thresholds from the audiogram were then added to the values in Table 2 above which is the summation of the ISO 40 Phon ELC correction values, and the dB HL to dB SPL transfer functions. This produces a measure of hearing in terms of the relative perceived loudness of stimuli at each of the discrete frequencies. The values were expressed in dB SPL so that the desired equalisation frequency response could be determined within the 24 dB SPL range of the graphic equaliser.

(vi) The baseline value was then subtracted from each transformed threshold, and its result then multiplied by the 0.4 gain rule. This process is repeated for each frequency of each ear.

(vii) These values were then used to manually set the graphic equaliser with the left ear's required equalisation response (REQ) used in the left channel, and the right ear's REQ used in the right channel of the equaliser.

Example 2

The audiogram for the participant chosen to demonstrate how the TMP1 accounts for a steeply-sloping asymmetrical hearing loss (see Example 1 above), was also chosen to demonstrate how the TRP algorithm modifies the intensity of the audio signal at selected frequencies to provide intermittent masking of the tinnitus. Tables 3 and 4 below show the calculations at each frequency for the left and right ears respectively using the TRP algorithm above. The baseline calculation was made as follows:

$$\text{Baseline} = 0.5\ (A - B) + B$$
$$= [0.5(L\ SPL_{10} + L\ SPL_{12}) - 0.5(R\ SPL_{0.5} + R\ SPL_{0.75})] \times$$
$$0.5 + 0.5(R\ SPL_{0.5} + R\ SPL_{0.75})$$
$$= [0.5(89.5 + 91) - 0.5(1.5 + 8.5)] \times$$
$$0.5 + 0.5(1.5 + 8.5)$$
$$= (90.25 - 5) \times 0.5 + 5$$
$$= 47.625$$

TABLE 3

| | | | Corrections and Calculations | | | | | |
|---|---|---|---|---|---|---|---|---|
| L Freq. (Hz) | P's dB HL | P's SPL = | ELC & SPL transfer functions | = | −Baseline | = | ×0.4 | = REQ |
| 250 | 5 | | 23.5 | 28.5 | 47.625 | −19.15 | ×0.4 | −7.66 |
| 500 | −10 | | 7.5 | −2.5 | 47.625 | −50.15 | ×0.4 | −20.06 |
| 750 | 2.5 | | 5.5 | 8 | 47.625 | −39.65 | ×0.4 | −15.86 |
| 1000 | 15 | | 7 | 22 | 47.625 | −25.65 | ×0.4 | −10.26 |
| 1500 | 25 | | 6.5 | 31.5 | 47.625 | −16.15 | ×0.4 | −6.46 |
| 2000 | 40 | | 7 | 47 | 47.625 | −0.65 | ×0.4 | −0.26 |
| 3000 | 65 | | 5.5 | 70.5 | 47.625 | 22.85 | ×0.4 | 9.14 |
| 4000 | 60 | | 2.5 | 62.5 | 47.625 | 14.85 | ×0.4 | 5.94 |
| 6000 | 60 | | 16.5 | 76.5 | 47.625 | 28.85 | ×0.4 | 11.54 |
| 8000 | 60 | | 21 | 81 | 47.625 | 33.35 | ×0.4 | 13.34 |
| 10000 | 80 | 89.5 | 16.5 | 96.5 | 47.625 | 48.85 | ×0.4 | 19.54 |
| 12000 | 80 | 91 | 13 | 93 | 47.625 | 45.35 | ×0.4 | 18.14 |

TABLE 4

| | | | Corrections and Calculations | | | | | |
|---|---|---|---|---|---|---|---|---|
| R Freq. (Hz) | P's dB HL | P's SPL = | ELC & SPL transfer functions | = | −Baseline | = | ×0.4 | = REQ |
| 250 | 20 | | 23.5 | 43.5 | 47.625 | −4.15 | ×0.4 | −1.66 |
| 500 | −10 | 1.5 | 7.5 | −2.5 | 47.625 | −50.15 | ×0.4 | −20.06 |
| 750 | 0 | 8.5 | 5.5 | 5.5 | 47.625 | −41.12 | ×0.4 | −16.85 |
| 1000 | 5 | | 7 | 12 | 47.625 | −35.65 | ×0.4 | −14.26 |
| 1500 | 0 | | 6.5 | 6.5 | 47.625 | −41.15 | ×0.4 | −16.46 |
| 2000 | 15 | | 7 | 22 | 47.625 | −25.65 | ×0.4 | −10.26 |
| 3000 | 45 | | 5.5 | 50.5 | 47.625 | 2.85 | ×0.4 | 1.14 |
| 4000 | 30 | | 2.5 | 32.5 | 47.625 | −15.15 | ×0.4 | −6.06 |
| 6000 | 30 | | 16.5 | 46.5 | 47.625 | −1.15 | ×0.4 | −0.46 |
| 8000 | 20 | | 21 | 41 | 47.625 | −6.65 | ×0.4 | −2.66 |
| 10000 | 60 | | 16.5 | 76.5 | 47.625 | 28.85 | ×0.4 | 11.54 |
| 12000 | 75 | | 13 | 88 | 47.625 | 40.35 | ×0.4 | 16.14 |

Figure 4:
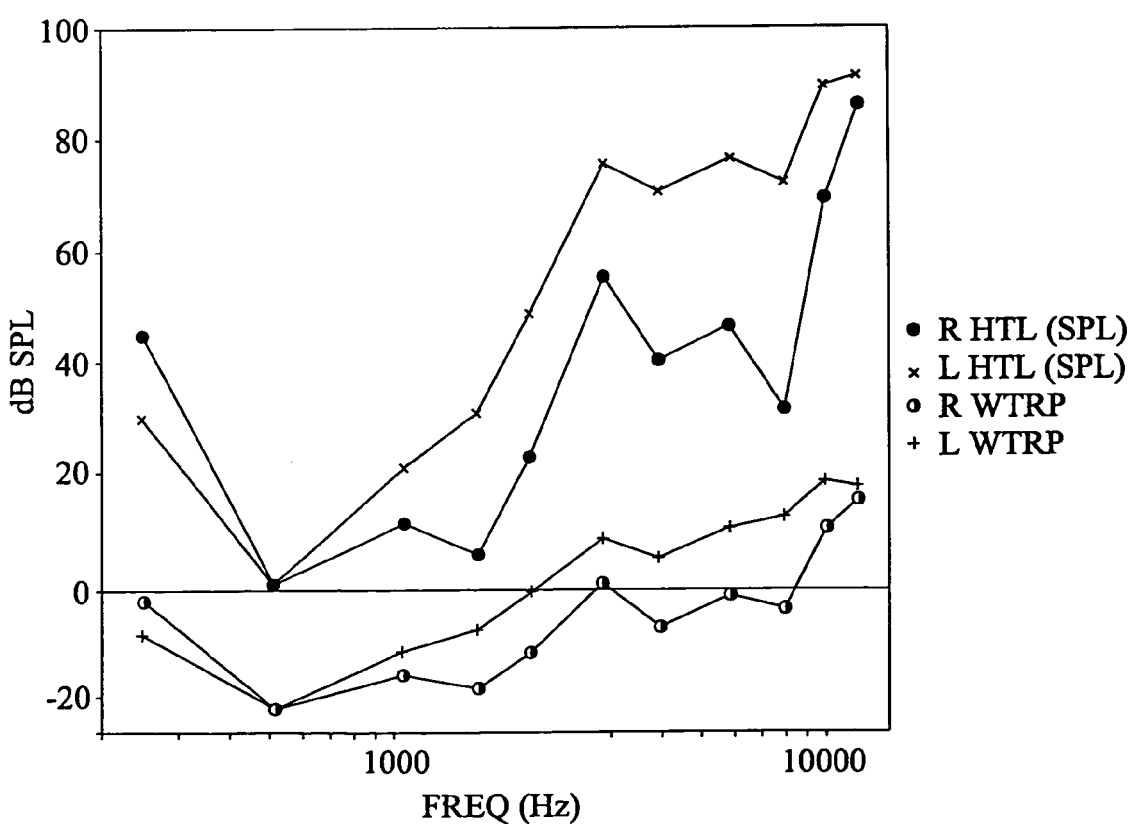
FIG. 4 is a graphical representation of the same patient's hearing thresholds and their required equalisation curves calculated using a second embodiment of the masking algorithm.

The REQ equalisation curves for both ears are illustrated graphically in FIG. 4. A comparison of FIG. 4 with FIG. 2 will confirm that the patient's right and left hearing thresholds [HTL(SPL)] curves are identical.

A second clinical study was conducted in which 90 people who suffer from tinnitus participated. The participants were allocated with block randomization into one of four treatment groups: one group to test a second generation total masking algorithm (TMP2), one to test the tinnitus retraining algorithm (TRP), one to empirically measure the current TRT approach of using low-level broadband noise stimulants, and a quasi-control group to receive counselling alone. The second study exceeded expectations, with dramatic levels of habituation experienced by more than three-quarters of the participants using spectrally modified music. The adoption of bibliotherapy and TRT-style counselling resulted in significant improvements in clinical outcomes for all treatment groups. However, counselling alone appeared to be insufficient treatment for most participants. An important finding was that the TRP group experienced the greatest mean improvements in tinnitus distress. The TMP2 stimulus group initially displayed a more rapid improvement, but the more gradual gains of the TRP group were sustained for longer, and ultimately were superior. There was little difference between the noise and counselling alone groups at post therapy and follow-up, although the mean improvements experienced by the counselling alone group were ultimately not statistically significant. While all treatment groups recorded mean reductions in tinnitus distress over therapy, the two music groups ultimately appeared to be the most effective. Approximately three-quarters of the two music group participants experienced significant habituation to their tinnitus (TMP2=78.6%, TRP=75%).

There were substantial reductions in hyperacusis scores for both music groups, and a slight reduction for the noise group. The group without acoustic stimulation (Counselling-only) displayed an increase in hyperacusis over the same period, strongly indicating that the provision of acoustic stimulation was a key ingredient in the hyperacusis improvements. The music group participants often reported that their hyperacusis levels tended to improve faster than their tinnitus perception.

The clinical studies therefore suggest that total masking with music is more effective to facilitate a rapid improvement in distress and relaxation levels, despite the fact that intermittent masking with music eventually proved to be more effective on several measures. This indicates that a two-stage approach might be most efficient, whereby patients initially should employ a total masking algorithm to give a stronger sense of relief and control, then later switch to intermittent masking to remove the tinnitus detection.

In the clinical studies, pre-recorded music was spectrally modified using the predetermined masking algorithms, and re-recorded on audio cassette tapes for participants' use. This approach is unlikely to be acceptable for widespread clinical use, in view of the potential copyright infringement problems in some states or countries. Purchase of the rights to re-record music from selected recording companies is one means of circumventing this, or the commissioning of recordings specifically for this purpose. In one embodiment it is proposed to provide a programmable "black box" device for use by private practitioners. The device thus envisaged can be programmed by a qualified audiologist to account for each individual's tinnitus and hearing loss characteristics, using the tinnitus masking algorithms and clinical protocols developed by the inventor. In one embodiment, the device may take the form of a musician's hearing aid-type device designed to spectrally modify the audio signal as it enters the wearer's ears. A more preferred embodiment is to provide the device in the form of a "black box" which can be employed in conjunction with a PMP and has an input adapted to connect to the audio output headphone jack on the PMP. The device would have a standard headphone jack to which a conventional PMP headphone can be connected. In an alternative embodiment, a modified sound recording is automatically generated in the audiologist's clinic, tailored to the patient's audiometric configuration, using software accessed via the World Wide Web.

Figure 5:
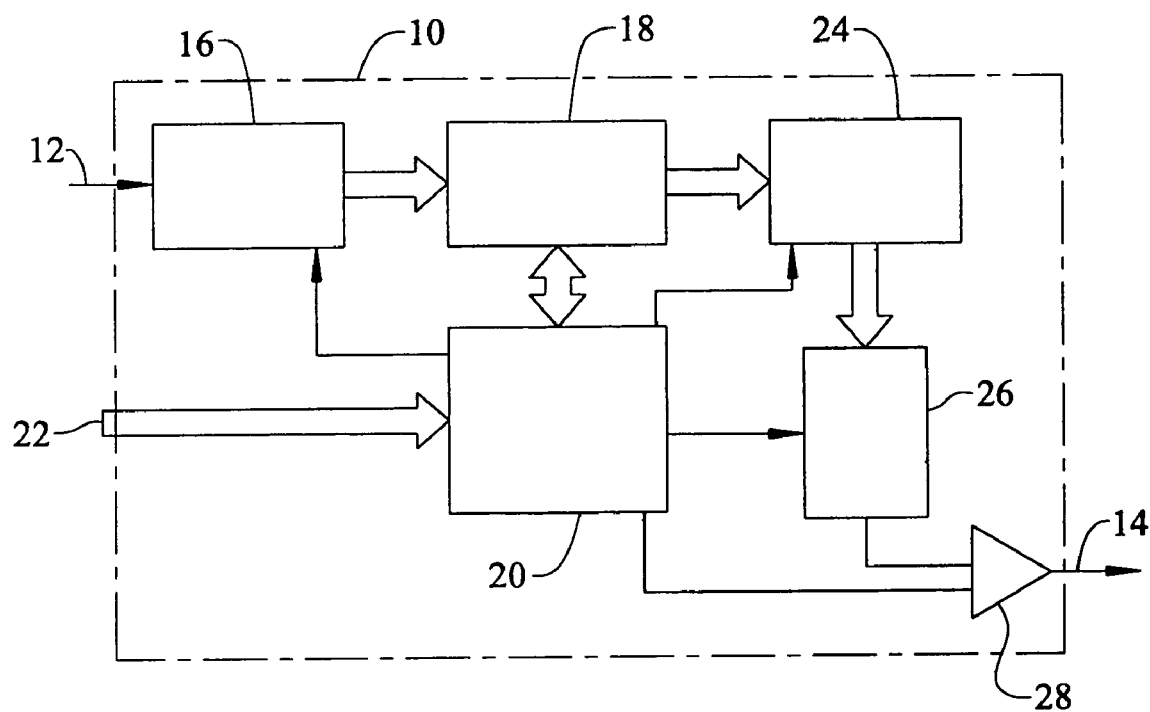
FIG. 5 is a schematic block diagram of a possible embodiment of a tinnitus rehabilitation device in accordance with the invention.
Figure 6A:
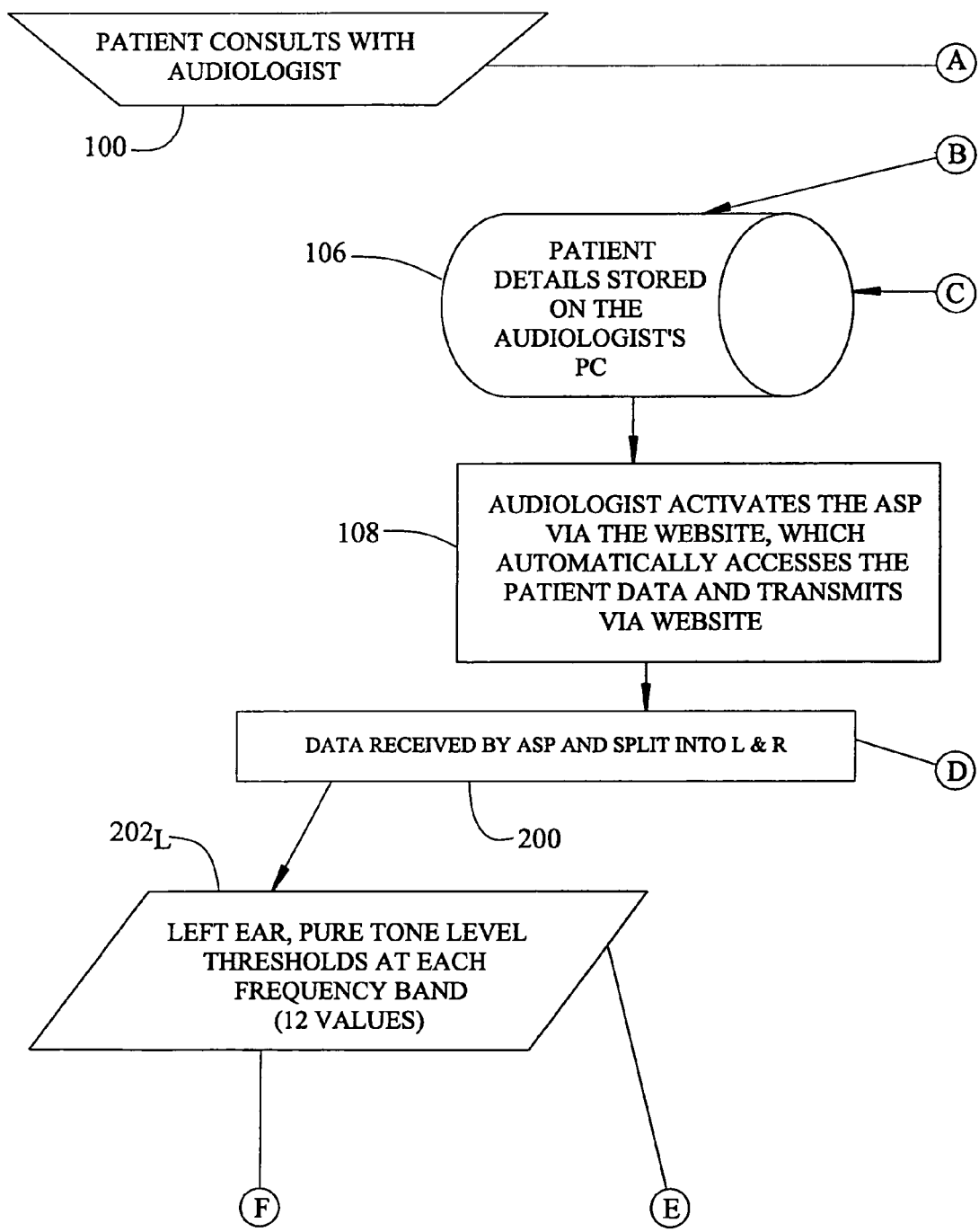
FIGS. 6 and 7 are flowcharts illustrating a preferred method of providing a tinnitus rehabilitation sound recording in accordance with the present invention.
Figure 6B:
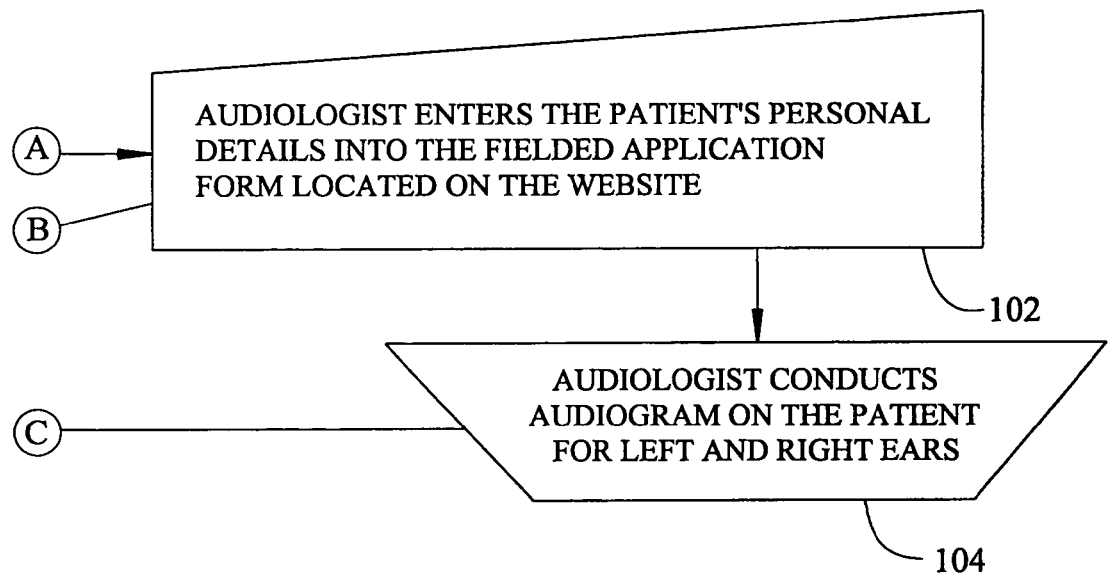
Figure 6C:
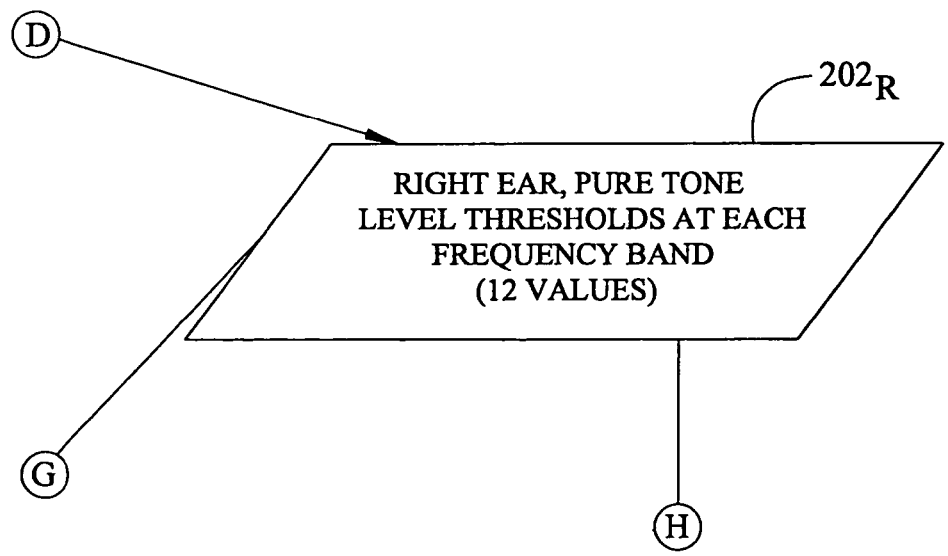
Figure 6E:
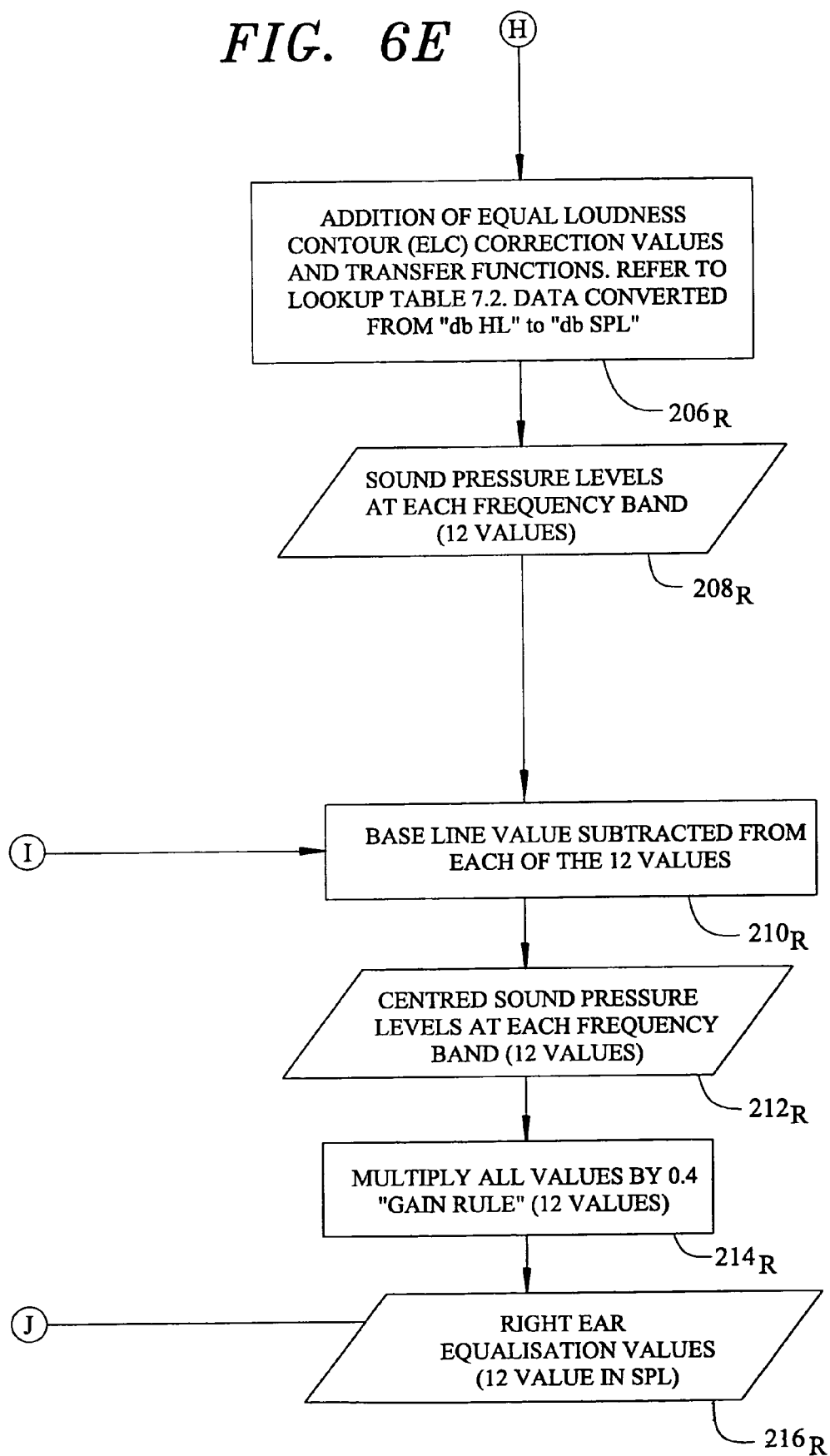
Figure 7A:
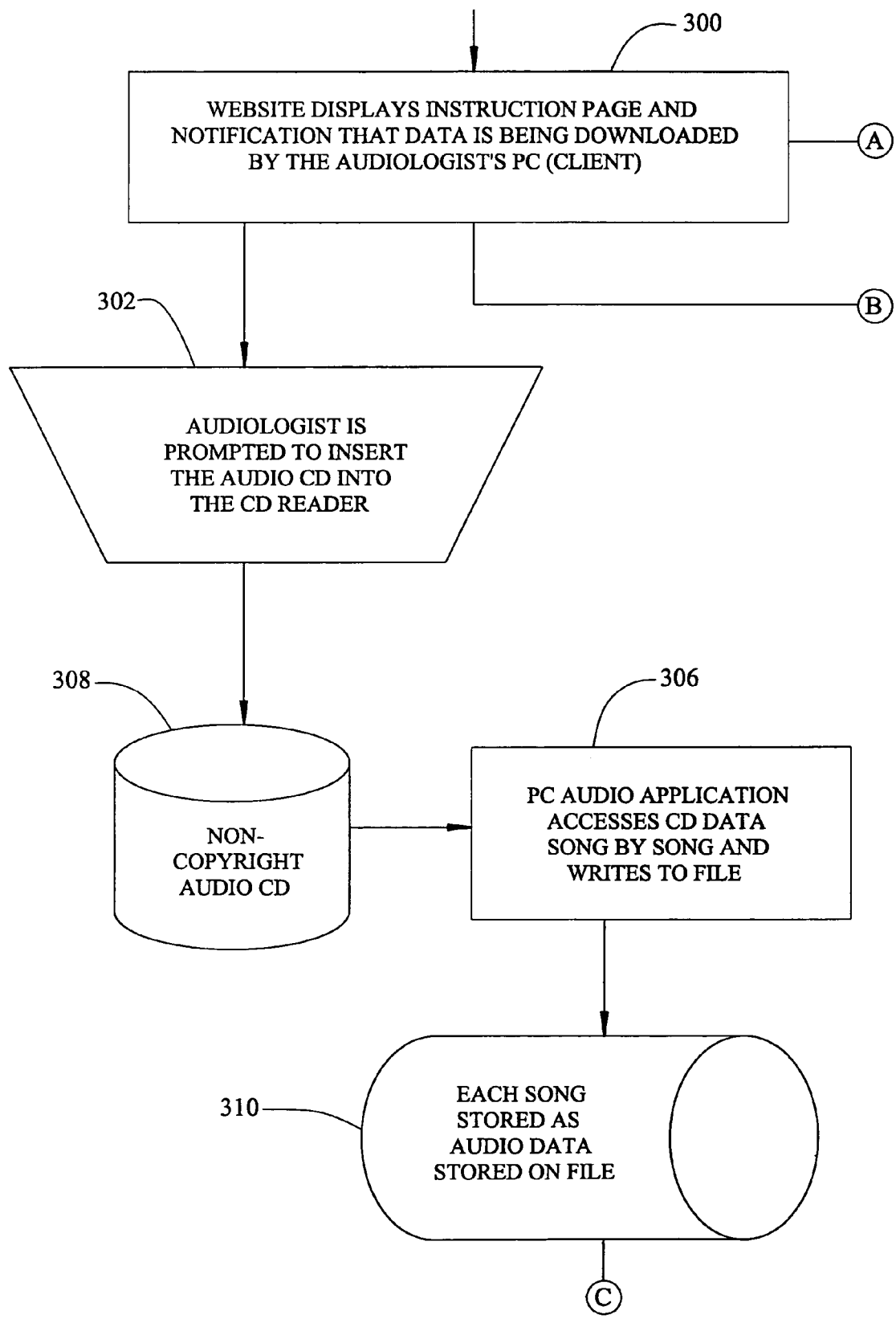
Figure 7B:
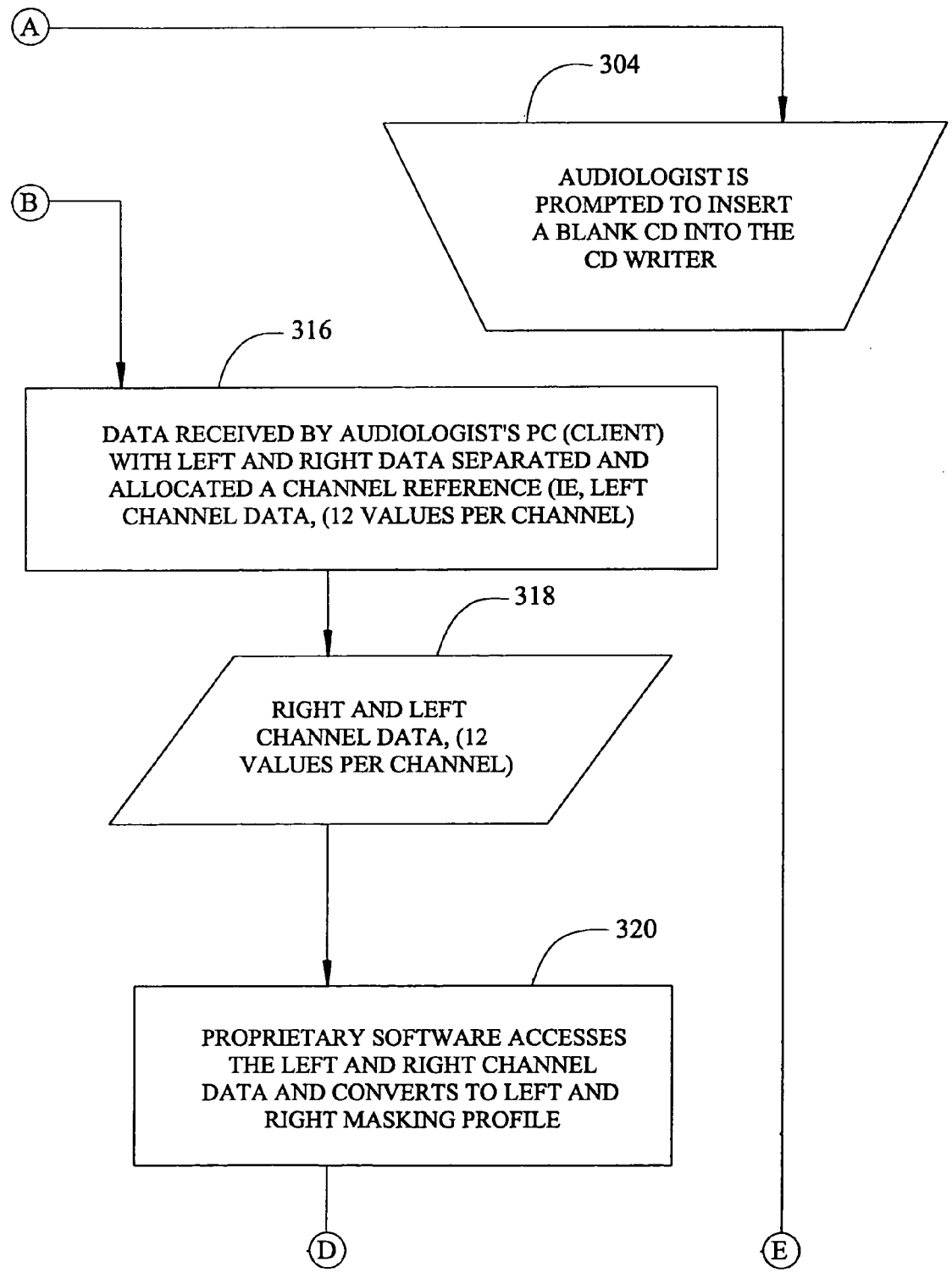
Figure 7C:
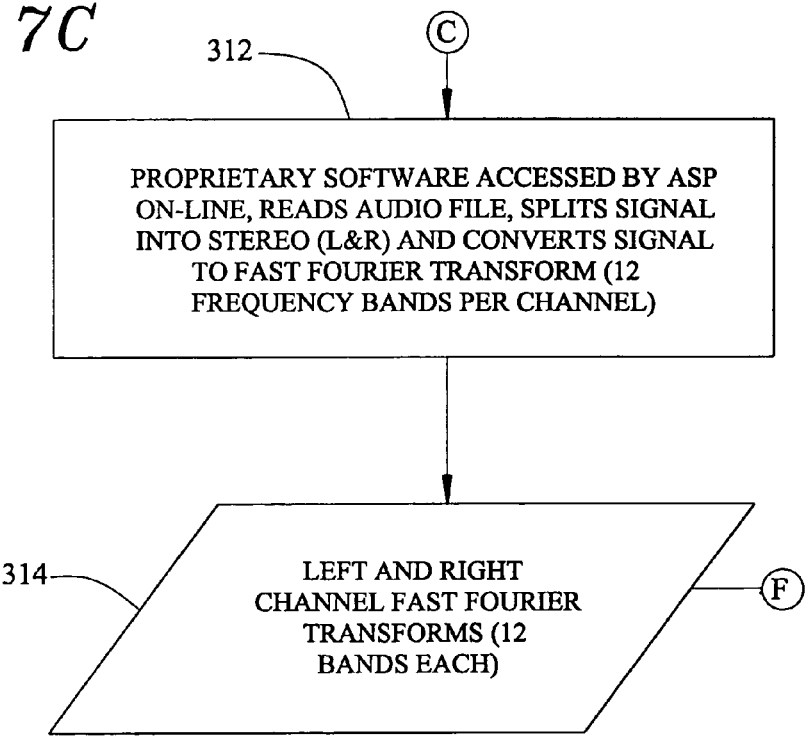
Figure 7D:
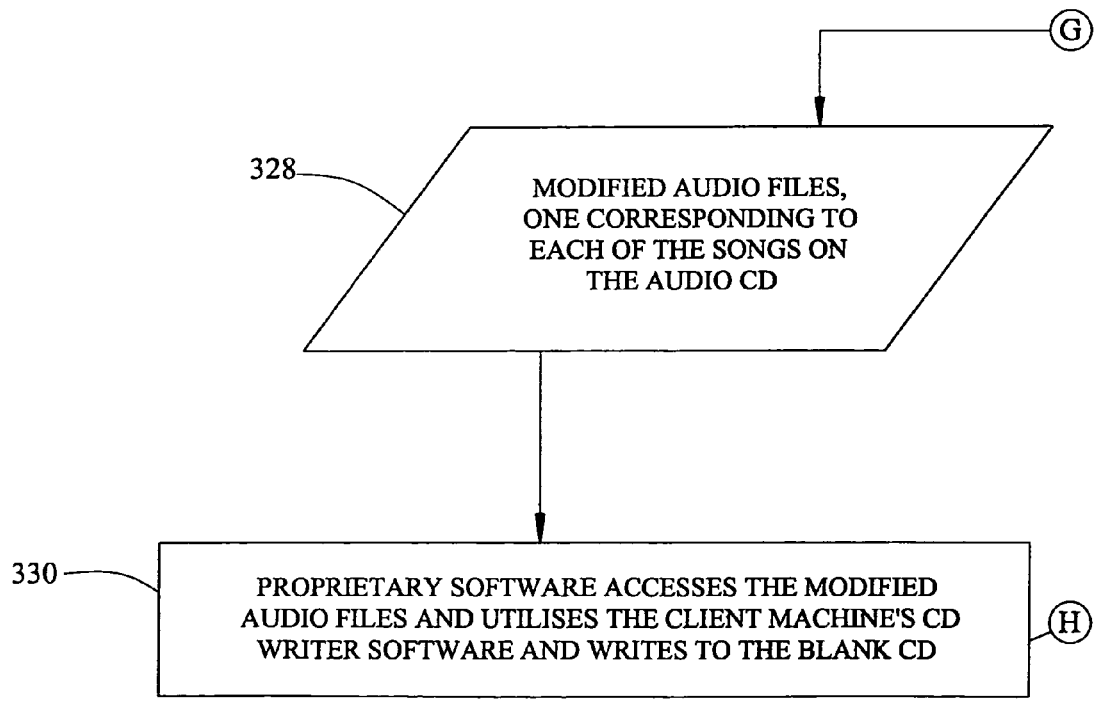

FIG. 5 illustrates in schematic block diagram form a possible embodiment of a tinnitus rehabilitation "black box" device. The device 10 has an input 12 adapted to receive a two-channel stereo signal from the headphone output jack of a PMP. The device 10 also has an output 14 which provides a two-channel stereo signal, spectrally modified by a predetermined masking algorithm programmed into the device 10, which is suitable for listening to through a conventional PMP headphone. Preferably, the device 10 employs digital signal processing, and therefore the left and right input audio analog signal is converted to digital format in an analog to digital converter (ADC) 16. The digital output signal of ADC 16 is then sent to a digital filter 18 which filters the digitised audio signal in accordance with a predetermined masking algorithm. The digital filter 18 modifies the intensity of the audio signal at selected frequencies in accordance with the masking algorithm.

The filter characteristic of the digital filter 18 may be programmed manually using thumbwheels. However, more preferably the digital filter 18 is programmed electronically by means of a microprocessor-based controller 20 having a communications port 22 that may be connected to a desk top computer. Using a custom-designed software program which accompanies the device 10, an audiologist or other hearing aid dispenser can program the device 10 by means of a graphic user interface (GUI) which facilitates the input of the required clinical data into the non-volatile memory of the controller 20. Thus, for example, the clinical audiologist would simply enter the patient's purr tone hearing level thresholds at each of the 10 discrete frequencies from 0.25 to 12 kHz. The audiologist may also be required to enter the two adjacent least hearing loss frequencies (B) the hearing threshold at the frequency of tinnitus pitch match (A) and/or the two adjacent greatest hearing loss frequencies (C). Either the software or the controller 20 will then use these figures to calculate the baseline value, and employ the predetermined masking algorithm to calculate the required equalisation values. These values are employed by the controller 20 to set the filter constants at each frequency in the digital filter 18.

The device 10 may also include an additional signal processing means 24, which is also under control of the controller 20, for providing further spectral modification of the digital audio signal after filtering by the digital filter 18. The spectrally modified audio signal is then converted back to analog format in a digital to analog converter (DAC) 26. An amplifier 28 may be provided to control the amplitude of the analog output signal provided at the output 14 of the device. It will be understood that each of the digital components of the device 10 may be integrated into a single integrated circuit, so that the dimensions of the device 10 can be made quite small and the device therefore remains inconspicuous.

Further investigation has revealed that the proprietary algorithms or digital processing of the audio signal may be entirely software-based, facilitating the production of a stored music medium (compact disc or alternative format) for playback by the tinnitus sufferer on a standard personal sound reproduction system, such as a personal music player (PMP), with headphones. In this embodiment, the method of providing a tinnitus rehabilitation sound recording takes full advantage of the speed and economies provided by the Internet for fast digital communications and remote processing power. With no more than a desktop personal computer (PC) with CD-writing capability, the ability to provide a customised tinnitus rehabilitation sound recording can be placed at the fingertips of the audiologist. By utilising the reach of the World Wide Web and developing an application service provider (ASP), (also described as "on-line operating software"), the method can be extended to provide tinnitus relief and treatment to a global marke. FIGS. 6 and 7 illustrate in flowchart form a preferred method of providing a tinnitus rehabilitation sound recording utilising the World Wide Web and the services of an ASP.

The process commences in the audiologist's clinic where the patient consults 100 with the audiologist. The audiologist enters 102 the patient's personal details into the appropriate fields in an application form located on a proprietary website. The audiologist then conducts 104 an audiogram on the patient's left and right ears. The audiogram is converted into an appropriate digital format and stored 106 on the audiologist's PC. The audiologist may then activate 108 the application service provider (ASP) via the website, which automatically accesses the patient data, including the digital audiogram, and transmits it via the website to the ASP.

Data is received 200 by the ASP and split into left and right ear processing channels. A central processing server (accessed via the ASP) houses the software containing the proprietary algorithms for converting the patient data to a digital filtering format herein referred to as a Masking Profile. This Masking Profile is then transmitted back to the audiologist's PC. The central processing server uses the digital audiogram to determine $202_L$, $202_R$ the pure tone level thresholds at each of the predetermined frequencies for the left and right ears. The software ascertains 204 the two adjacent greatest hearing loss frequencies in the greatest hearing loss ear, and also the two adjacent least hearing loss frequencies in the least hearing loss ear. In each of steps $206_L$, $208_L$, $210_L$, $212_L$, $214_L$, $216_L$ and $206_R$, $208_R$, $210_R$, $212_R$, $214_R$, $216_R$ the tinnitus retraining protocol algorithm is applied to the left ear and right ear levels respectively, as is illustrated graphically in Tables 3 and 4 above.

In steps 218, 220 and 222 the baseline value is calculated, which is subtracted from each of the transformed threshold values for the left and right ears at $210_L$, $210_R$. The left and right ear Required Equalisation Response (REQ) values are then transmitted 224 to the audiologist's PC via the ASP website. The website, which is visible on the audiologist's PC, notifies 226 the audiologist that the REQ values are being downloaded onto the audiologist's PC, and also prompts 302 the audiologist to insert a music CD into a CD player connected to the PC. The audiologist is also prompted 304 to insert a blank CD into the CD writer connected to his PC. It is to be understood that any suitable audio recording may be employed, preferably a music recording, stored on any suitable storage medium, such as a compact disc, audio cassette or MP3 card. Typically, the patient is offered a choice of music CD's, for which the appropriate copyright licence fees have been paid, to be used as the base recording. An audio software application on the audiologist's PC accesses 306 the CD recording 308 and stores 310 the audio data to a file in the memory of the PC.

Proprietary software accessed by the ASP online reads the audio files stored in the PC, splits the signal into left and right stereo signals and converts them to Fast Fourier Transform 312 (FT) format 314. Meanwhile, the REQ data received by the audiologist's PC is allocated 316 a channel reference (ie left channel data and right channel data 318). The software then converts 320 this left and right channel data into left and right Masking Profiles 322 respectively. Software provided on the audiologist's PC accesses 324 and applies the Masking Profiles to the right and left FFT signals for each of the stored songs in order to produce the left and right channels of the spectrally modified music signal. Proprietary software 326 converts 326 the modified left and right signals back to the frequency domain for playback as a conventional audio file. The modified audio files 328, one corresponding to each of the songs on the original music CD, are then utilised 330 by the CD Writer Software stored in the audiologist's PC, and are written to a blank CD 332.

The advantage of using an ASP and the audiologist's PC is that the amount of data transmitted and the processing power required by the server is in relative terms, very low. It is the processing of the audio signal that requires the bulk of the processing power. Via this model that power is housed in the PC of the audiologist instead of the server. Processing time would be negligible and therefore the entire process could be encompassed in the one patient visit.

Transmission is either via e-mail using a secure line with encryption or via a password-restricted web page; only qualified audiologists having access. Additional security measures such as 'one-time-only-downloads' or limiting the time the data is available on the website are also possible.

The consultation can easily be held in conjunction with a therapy session with the audiologist, or as part of a coordinated therapy regime of on-going treatment. Possible revenue streams include the download of the proprietary software from the website and a royalty on each data download, ie. for each CD made (not per patient, as each patient may wish to modify more than one CD). The Internet website could also provide a number of other services to assist in the relief of and treatment of tinnitus and hyperacusis. Thus, while music is the preferred embodiment, CDs can also be produced using noise, environmental sounds, pure tones, or even speech signals if this is strongly preferred by the sufferer. The more computer-literate sufferers could enter their audiogram details without the help of an audiologist. When the audiologist or hearing aid dispenser does not have a CD burner, facility will be available for the CD to be produced at the ASP or other site, then posted to the clinic. As the data transmission speed of the Internet significantly increases, facility will be available for the processing of the audio signal to be performed within the ASP server if required.

Now that several embodiments of the tinnitus rehabilitation method and device have been described in detail, it will be apparent that the described method and device for providing relief for persons suffering from tinnitus has a number of significant advantages over prior art techniques, including the following:

(i) by facilitating the use of a personal music player with relaxing music, it is much more acceptable to patients than conventional hearing aid-style maskers;

(ii) it compensates for high frequency hearing loss which accompanies the tinnitus in approximately 80% of cases, thus providing the broadest spectrum of acoustic stimulation;

(iii) the masking algorithms developed to spectrally modify the masking/retraining audio stimuli correct for each individual's particular hearing loss configuration as well as accounting for the effects of loudness recruitment, thus enabling effective stimulation at a relaxing intensity level;

(iv) intermittent tinnitus masking with music can provide a form of systematic desensitisation to the disturbing effects of tinnitus; and, (v) spectrally modified sound recordings produced using the masking algorithms reduce tinnitus distress to the point where it was no longer significantly interfering with quality of life in more than 75% of trial participants. Significant reductions in MMLs were measured, and hyperacusis levels had significantly improved.

It will also be apparent to persons skilled in the audiological and electronics arts that numerous variations and modifications may be made to the described method and device, in addition to those already described, without departing from the basic inventive concepts. For example, a masking algorithm in accordance with the invention may be employed to set the frequency response of existing tinnitus maskers which use bands of noise, rather than music, to achieve similar results. Various types of noise, pure tones and speech could also be used in addition to music. The same masking algorithms may also be employed in existing wireless receiver devices, (such as the Starkey Silentia Set), or through hearing aid induction coil systems. Furthermore, the mathematical algorithms used for calculating the individual prescription of the audio signal may differ from the above described algorithms, and extra sounds may also need to be inserted. However, other embodiments of the invention would be consistent with the essential clinical technique that is intended to provide a modification of the intensity of audio signals to account for hearing levels, specifically for the relief and/or treatment of tinnitus and/hyperacusis. All such variations and modifications are to be considered within the scope of the present invention, the nature of which is to be determined from the foregoing description and the appended claims.

The invention claimed is:

1. A hearing aid for providing relief to a person suffering from the disturbing effects of tinnitus, the hearing aid comprising:
   a signal filter configured to spectrally modify at least a portion of an audio signal including peaks and troughs in accordance with a predetermined masking algorithm designed to modify at least one of the peaks and the troughs of at least a portion of the audio signal at selected frequencies,
   wherein said predetermined masking algorithm accounts for the basic audiometric configuration of the person whereby, in use at a comfortable listening level, when the spectrally modified audio signal is heard by the person during the peaks, the tinnitus is at least substantially obscured and the person perceives significant masking of the tinnitus, and during troughs, the person may occasionally perceive the tinnitus.

2. A hearing aid as defined in claim 1, wherein said signal filter is a programmable signal filter whereby, in use, the hearing aid can be programmed with a predetermined masking algorithm adapted to particular needs of the person suffering from tinnitus.

3. A hearing aid as defined in claim 2, wherein said predetermined masking algorithm is designed to modify the intensity of the audio signal across substantially a full spectral range of the audio signal.

4. A hearing aid as defined in claim 3, wherein said audio signal is a highly dynamic signal whose spectral content and intensity constantly varies over time.

5. A hearing aid as defined in claim 4, wherein the audio signal is a music signal.

6. A hearing aid as defined in claim 1, wherein said predetermined masking algorithm is partly tailored to a hearing loss characteristic of the person.

7. A hearing aid as defined in claim 6, wherein the predetermined masking algorithm is configured to modify spectral qualities of the audio signal so as to provide a relatively equal sensation level across a major portion of an audio spectrum in both ears.

8. A hearing aid as defined in claim 7, wherein said predetermined masking algorithm also incorporates a set of calibration figures for converting dB HL (Hearing Level) to dB SPL (Sound Pressure Level).

9. A hearing aid as defined in claim 8, wherein the predetermined masking algorithm is of the form:

| | |
|---|---|
| REQ = | M(SPL + ELC (F) − Baseline) |
| where REQ = | Required equalisation response of the Tinnitus Retraining Protocol |
| Baseline = | 0.5 (A − B) + B |
| A = | mean dB SPL at the two adjacent greatest hearing loss frequencies in the greatest hearing loss ear |
| B = | mean dB SPL at the two adjacent least hearing loss frequencies in the least hearing loss ear |
| SPL = | hearing thresholds (in dB HL) converted to dB SPL |
| ELC = | transfer values for 40 Phon Equal Loudness Contours |
| M = | gain multiplier 0.3 to 0.95 Preferably M = 0.4 |
| F = | a plurality of frequencies within the accepted range of normal human hearing. |

10. A method for providing relief to a person suffering from tinnitus, the method comprising:
   providing an audio signal including peaks and troughs;
   producing a treatment signal designed to modify at least one of peaks and troughs of at least a portion of the audio signal for providing at least intermittent masking of the tinnitus, wherein the treatment signal is configured to account for certain characteristics of the person; and
   modifying the audio signal by combining the audio signal with the treatment signal such that in use at a comfortable listening level, when the modified audio signal is heard by the person, the person may occasionally perceive the tinnitus.

11. The method of claim 10, wherein said audio signal is a dynamic signal whose spectral content and intensity varies over time.

12. The method of claim 10, wherein said audio signal is a music signal.

13. The method of claim 10, wherein the audio signal is stored in a hearing aid.

14. The method of claim 10, wherein the audio signal is stored in a device that is configured to communicate with a hearing aid.

15. The method of claim 14, wherein the device wirelessly communicates with the hearing aid.

16. A device for providing relief to a person suffering from tinnitus, the device comprising:
   a portion configured to spectrally modify at least a portion of an audio signal including peaks and troughs by combining the audio signal with a treatment signal,
   wherein the treatment signal is designed to modify at least one of the peaks and the troughs of at least a portion of the audio signal, and
   wherein the treatment signal accounts for certain characteristics of the person whereby, in use at a comfortable listening level, the person may occasionally perceive the tinnitus.

17. The device of claim 16, wherein the device is adapted to be used in conjunction with a conventional personal sound reproducing device with headphones.

18. The device of claim 16, wherein said audio signal is a dynamic signal whose spectral content and intensity varies over time.

19. The device of claim 16, wherein said audio signal is a music signal.

20. The device of claim 16, wherein the device is a hearing aid.

21. The device of claim 16, wherein the device is configured to communicate with a hearing aid.

22. The device of claim 21, wherein the device wirelessly communicates with the hearing aid.

23. A method for providing relief to a person suffering from tinnitus, the method comprising:
   providing a treatment signal;
   modifying the treatment signal by combining the treatment signal with a second signal that includes troughs and peaks;
   wherein the modified treatment signal at least intermittently relieves the perception of the tinnitus.

24. The method of claim 23, wherein said audio signal is a dynamic signal whose spectral content and intensity varies over time.

25. The method of claim 23, wherein said audio signal is a music signal.

26. The method of claim 23, wherein the audio signal provides a relaxing stimulus on at least one of a psychological, acoustic, and neural level.

27. The method of claim 23, wherein the modified treatment signal is provided to the person via an external device.

28. The method of claim 27, wherein the external device comprises headphones.

29. The method of claim 23, wherein the modified treatment signal is provided to the person via a hearing aid.

30. A device for providing relief to a person suffering from the disturbing effects of tinnitus, the device comprising:
   a signal filter configured to spectrally modify at least a portion of an audio signal including peaks and troughs in accordance with a predetermined masking algorithm designed to modify at least one of the peaks and the troughs of at least a portion of the audio signal at selected frequencies,
   wherein said predetermined masking algorithm accounts for the basic audiometric configuration of the person whereby, in use at a comfortable listening level, when the spectrally modified audio signal is heard by the person during the peaks, the tinnitus is at least substantially obscured and the person perceives significant masking of the tinnitus, and during troughs, the person may occasionally perceive the tinnitus; and
   wherein the device is configured to communicate with a hearing aid to provide the relief to the person suffering from tinnitus.

31. A device as defined in claim 30, wherein said signal filter is a programmable signal filter whereby, in use, the device can be programmed with a predetermined masking algorithm adapted to particular needs of the person suffering from tinnitus.

32. A device as defined in claim 31, wherein said predetermined masking algorithm is designed to modify the intensity of the audio signal across substantially a full spectral range of the audio signal.

33. A device as defined in claim 32, wherein said audio signal is a highly dynamic signal whose spectral content and intensity constantly varies over time.

34. A device as defined in claim 33, wherein the audio signal is a music signal.

35. A device as defined in claim 30, wherein said predetermined masking algorithm is partly tailored to a hearing loss characteristic of the person.

36. A device as defined in claim 35, wherein the predetermined masking algorithm is configured to modify spectral qualities of the audio signal so as to provide a relatively equal sensation level across a major portion of an audio spectrum in both ears.

37. A device as defined in claim 36, wherein said predetermined masking algorithm also incorporates a set of calibration figures for converting dB HL (Hearing Level) to dB SPL (Sound Pressure Level).

38. A device as defined in claim 37, wherein the predetermined masking algorithm is of the form:

| | |
|---|---|
| REQ = | M(SPL + ELC (F) − Baseline) |
| where REQ = | Required equalisation response of the Tinnitus Retraining Protocol |
| Baseline = | 0.5 (A − B) + B |
| A = | mean dB SPL at tbe two adjacent greatest hearing loss frequencies in the greatest hearing loss ear |
| B = | mean dB SPL at the two adjacent least hearing loss frequencies in the least hearing loss ear |
| SPL = | hearing thresholds (in dB HL) converted to dB SPL |
| ELC = | transfer values for 40 Phon Equal Loudness Contours |
| M = | gain multiplier 0.3 to 0.95 Preferably M = 0.4 |
| F = | a plurality of frequencies within the accepted range of normal human hearing. |

39. A device as defined in claim 30, wherein the device is configured to wirelessly communicate with the hearing aid.

* * * * *